United States Patent [19]

Parekh

[11] 4,105,708

[45] Aug. 8, 1978

[54] DIMETHOXYMETHYL DIETHOXYMETHYL GLYCOLURIL AND COATING COMPOSITIONS CONTAINING THE SAME AS A CROSS-LINKING AGENT

[75] Inventor: Girish Girdhar Parekh, Stamford, Conn.

[73] Assignee: American Cyanamid Company, Stamford, Conn.

[21] Appl. No.: 721,008

[22] Filed: Sep. 7, 1976

[51] Int. Cl.$^2$ .................. C08G 12/28; C08L 61/26
[52] U.S. Cl. .................. 260/849; 204/181 C; 252/182; 260/29.4 R; 260/29.4 UA; 260/31.4 R; 260/334 R; 260/33.6 R; 260/850; 260/851; 428/436; 428/460; 428/528; 428/530; 548/304
[58] Field of Search .......... 260/849, 850, 851, 67.5, 260/68, 29.4 R, 29.4 UA, 309.7; 252/182; 548/304

[56] References Cited

U.S. PATENT DOCUMENTS 4,009,134   2/1977   Elmer ..................... 260/29.3

FOREIGN PATENT DOCUMENTS 1,486,213   5/1967   France.
  956,741   7/1962   United Kingdom.
1,146,858   7/1966   United Kingdom.

OTHER PUBLICATIONS

Chem. Abstracts, vol. 83 1975 (p. 18282b).

*Primary Examiner*—Theodore E. Pertilla
*Attorney, Agent, or Firm*—James T. Dunn; John L. Sullivan

[57] ABSTRACT

A normally liquid substantially fully methylolated, substantially fully mixed alkylated glycoluril derivative consisting essentially of dimethoxymethyl diethoxymethyl glycoluril is a highly effective cross-linking agent for both water-based and organic solvent-based resin coating compositions.

3 Claims, No Drawings

DIMETHOXYMETHYL DIETHOXYMETHYL GLYCOLURIL AND COATING COMPOSITIONS CONTAINING THE SAME AS A CROSS-LINKING AGENT

CROSS-REFERENCES TO RELATED APPLICATIONS

Reference is made to my U.S. patent application, Ser. No. 654,446, filed Feb. 2, 1976, now abandoned my U.S. application Ser. No. 665,488, filed Mar. 10, 1976, and my U.S. application, Ser. No. 674,797, filed Apr. 8, 1976, all of which patent applications disclose the use of certain glycoluril derivatives in various coating compositions. Each of these pending U.S. patent applications are incorporated herein by reference.

BACKGROUND OF THE INVENTION

Cross-linking agents have been utilized over a long period of time in coating compositions that are useful as organic metal finishes which finishes have been commercially available for a substantial plurality of years. Many years ago coatings were prepared from such natural materials as linseed oil which were later superseded in time by synthetic polymeric materials. Frequently, these earlier materials were dissolved in organic solvents and deposited by any of a plurality of conventional methods onto the metallic substrates and were dried or baked to produce the desired coating on the metal substrate. Some of these earlier coating compositions were not as hard nor as chemically resistant (solvents, acids, etc.) as desired. As a consequence, further developments produced blends of cross-linkable polymeric materials which were used in conjunction with a cross-linking agent. When the combination was used as a coating on a metallic substrate and then baked so as to convert the cross-linkable polymeric material and the cross-linking agent to the thermoset state, there is provided a hard, chemical resistant film. In more recent times, because of the ecology considerations, the organic solvent systems have been replaced, at least in part, by aqueous systems which provide an aqueous dispersion of the blended materials.

FIELD OF THE INVENTION

The present invention is in the field of a class of novel cross-linking agents which are normally liquid, substantially fully mixed-alkylated, substantially fully methylolated glycoluril derivatives. These glycoluril derivatives will be described in greater detail hereinbelow and are useful in combination with a host of non-gelled polymeric materials that are cross-linkable although sometimes normally non-self-cross-linkable materials containing certain reactive groups can be used. These normally liquid fully mixed-alkylated, fully methylol glycoluril derivatives are dispersible in both aqueous systems and organic solvent systems and as a consequence, display great versatility. Certain glycoluril derivatives such as the tetrakismethoxymethyl glycoluril is a solid material melting at about 114–118° C. and is a solid product which can be used only with disadvantages in water or solvent based coatings. The mixed ethers of the methylolated glycolurils of the present invention, being liquid, are easy to formulate and handle in large scale paint manufacture.

DESCRIPTION OF THE PRIOR ART

The most pertinent prior art known is the British Pat. No. 1,146,858 and its French counterpart No. 1,486,213. No U.S. counterpart patent is presently known to exist.

SUMMARY OF THE INVENTION

This invention relates to normally liquid, substantially fully mixed-alkylated, substantially fully methylolated glycoluril derivatives having a degree of methylolation, on average, of at least 3.70; having a degree of methylation, on average, of between about 0.9 and 3.60; having a degree of higher alkylation selected from ethylation, propylation and butylation, on average, correspondingly between about 2.80 and 0.40 and having a degree of total alkylation, on average, between about 3.70 and 4.00. The invention also relates to the process of preparing these glycoluril derivatives. The preferred degree of methylolation, on average, is the same, namely, at least 3.70. However, the preferred degree of methylation, on average, is between about 1.4 and 3.2. By the same token, the degree of higher alkylation selected from ethylation, propylation and butylation, on average, will correspondingly be between about 2.3 and 0.8. The degree of total alkylation, on average, remains between about 3.70 and 4.00. These mixed full ethers will be used as cross-linking agents with water-dispersible or organic solvent dispersible, non-gelled, cross-linkable (under normal baking conditions) polymeric materials which polymeric materials will contain as reactive groups any one or more of carboxyl groups, alcoholic hydroxyl groups or amide groups wherein the amount of said groups is at least about 0.5%, by weight, and not more than about 20%, by weight, based on the total weight of said polymeric material. If the polymeric material is a normally non-self-cross-linkable polymeric material, it will generally be necessary to use an acid catalyst in an amount varying between about 0.05% to about 5.0%, by weight, based on the total weight of the cross-linking agent and the cross-linkable polymeric material. The reactive groups referred to hereinabove in the polymeric material are heat reactive with the glycoluril cross-linking agents and the normal baking conditions for these coatings are generally about 200° C. or less for about 30 minutes or less.

In the last ten years, dramatic changes have taken place in the organic coating technology. There has been increased emphasis on pollution-free coating systems, such as aqueous emulsion, water-borne coatings, electro coatings, power coatings and ultra-violet light curable coatings. The existing cross-linking agents based on melamine, the guanamines, including benzoguanamine, or urea and substituted ureas do not fill all of the needs of the present coating market.

The normally liquid, substantially fully mixed-alkylated, substantially fully methylolated glycolurils of the present invention are a new class of cross-linking agents, the starting material of which is glycoluril, per se, which is also known as acetylene diurea which is prepared by reacting two moles of urea with one mole of glyoxal. The precise chemical name for glycoluril is tetrahydroimidazo-(4, 5-d) imidazole 2, 5(1H, 3H)-dione. The glycoluril can be fully methylolated by reacting one mole of glycoluril with four moles of formaldehyde. The resulting product is identified as tetramethylol glycoluril. The tetramethylol glycoluril is then reacted with a selected amount of methanol so as to partially methylate the fully methylolated glycoluril which is then followed by alkylation with a higher aliphatic monohydric alcohol containing from two to four carbon atoms. These monohydric alcohols may be primary or secondary alcohols. These higher monohydric aliphatic alcohols containing from two or four carbon atoms may be ethanol, n-propanol, isopropanol, n-butanol, isobutanol and the like. It is sometimes advantageous to fully methylate the tetramethylol glycoluril and then by use of a transetherification reaction incorporate the desired measure of ethanol, propanol or butanol into the glycoluril derivative.

These fully etherified, fully methylolated glycoluril derivatives are not considered to be resinous materials since they are, as individual entities, simple pure compounds or mixtures of simple pure compounds but they are potential resin-forming compounds which enter into chemical reaction with certain ionic water-dispersible, non-gelled polymeric materials when subjected to heat and particularly when subjected to heat under acidic conditions. The concept of the degree of methylation or more broadly alkylation, on average, and the concept of the degree of methylolation, on average, will be discussed hereinbelow in order that this concept may be fully understood.

Theoretically, it is possible to methylolate glycoluril fully, that is, to produce tetramethylol glycoluril. However, frequently, in a commercial composition purporting to be tetramethylol glycoluril, when analyzed, may show a fractional degree of methylolation. It is well recognized that fractional methylolation is not considered to be possible. As a consequence, when a composition contains on analysis a degree of methylolation of 3.70, 3.80, or 3.90, it has to be recognized that this is but an average degree of methylolation of the glycoluril compound and establishes logically that the aforementioned methylol composition is composed of a mixture of a preponderant amount of tetramethylol glycoluril with comparatively minor amounts of trimethylol glycoluril and, perhaps, insignificant amounts including traces of such derivatives as dimethylol glycoluril and even monomethylol glycoluril. The same concept of averages is also applicable to the alkylation or etherification of the tetramethylol glycoluril composition. There cannot be, based on present reasoning, a fractional alkylation and, as a consequence, when on analysis, a given composition shows that the degree of methylation is, on average, between about 0.9 and 3.60 and that the higher alkylation has an average degree of ethylation, propylation and/or butylation, on average, correspondingly between about 2.80 and 0.40, it must be concluded that there is present in such a composition a plurality of the mixed ethers of the tetramethylol glycoluril. For instance, there may be present some monomethyl ether, triethyl ether of tetramethylol glycoluril, some dimethyl ether, diethyl ether of tetramethylol glycoluril, some trimethyl ether, monoethyl ether of tetramethylol glycoluril. There may even be traces of the tetramethyl ether of tetramethylol glycoluril. There may also be present with the varying methyl ethers of tetramethylol glycoluril varying mono, di and tri ethyl ethers, mono, di and tri propyl ethers and mono, di and tri butyl ethers of tetramethylol glycoluril. One could, in fact, produce a monomethyl ether, monoethyl ether, monopropyl ether, monobutyl ether of tetramethylol glycoluril which could be classed as a tetramixed-alkylated derivative. It is generally preferred, however, to make use of only one higher monohydric alcohol containing from two to four carbon atoms with the methyl alcohol in making a mixed full ether of the tetramethylol glycoluril. The dimixed-alkylated products are therefore, preferred although one could prepare and utilize the trimixed-alkylated derivatives as well as the tetramixed-alkylated derivatives.

In order that the concept of the present invention may be more completely understood, the following examples are set forth in which all parts are parts by weight unless otherwise indicated. These examples are set forth primarily for the purpose of illustration and any specific enumeration of detail contained therein should not be interpreted as a limitation on the case except as is indicated in the appended claims.

Preparation of Glycoluril

Into a suitable reaction vessel equipped with stirrer, thermometer and reflux condenser, there was introduced 765 parts of urea and 875 parts of water. To this slurry, 282 parts of concentrated sulfuric acid was charged and the mixture was heated to 70° C. At 70° C, 605 parts of glyoxal (40% aqueous solution and free from formaldehyde) were added slowly to the clear solution such that the reaction temperature was maintained between 75°–80° C. After the addition of the glyoxal, the reaction mixture was held at 75° C. for one hour and then cooled. The separated crystalline glycoluril was filtered and washed with water and with a dilute caustic aqueous solution. The glycoluril obtained after drying has a melting point of 298°–300° C. and the yield was 88% (525 parts).

Preparation of Tetramethylol Glycoluril

Into a suitable reaction vessel equipped with a stirrer, thermometer and reflux condenser, there was introduced 688 parts (10 moles) of aqueous formaldehyde (44%), and the pH was adjusted to 8.7 with 22 parts of 0.5 N NaOH solution. To this solution, there was added 284 parts (2 moles) of glycoluril at 40° C. During the reaction, the temperature was allowed to rise up to 55° C. At this stage, most of the glycoluril has gone into solution. After about 15 minutes, the pH was adjusted to 8.0 with five parts of 0.5 N NaOH. A clear, pale yellow colored solution was obtained. The clear solution was distilled at 50° C., under reduced pressure to remove water, until the reaction vessel content was about 640 parts. The syrup in the vessel was poured into 800 parts of methanol. The white crystalline precipitate was filtered and dried. The total yield of the tetramethylol glycoluril was 483 parts (92%) and melting point of 132°–136° C.

Preparation of Dimethoxymethyl Diethoxymethyl Glycoluril

Into a suitable reaction vessel, equipped as before, there was charged 320 parts (10 moles) of methanol, 460 parts of ethanol (10 moles), and 20 parts of 70% concentrated nitric acid. To this acidic alcoholic mixture, there was charged 262 parts (1 mole) of tetramethylol glycoluril and the reaction mixture was heated to 40° C., with stirring. In about 20 minutes, all of the tetramethylol glycoluril had gone into solution. When the reaction mixture became clear, it was cooled to 22° C. and 45 parts of 20% sodium hydroxide solution were added to neutralize the reaction mixture to a pH of 7-8. The neutralized clear solution was heated slowly to 105° C. under reduced pressure to remove substantially all of the alcohol-water mixture. The resultant syrup was filtered hot at 80° C. to remove the inorganic salts and other impurities. The yield of the syrupy dimethoxymethyl diethoxymethyl glycoluril was 320 parts. The structure of this product was confirmed by nuclear magnetic resonance spectroscopy. The pan solids were 95.0% and the foil solids were 98.5%. The Gardner-Holdt viscosity was $Z_3$–$Z_4$ (at 25° C.). The product was soluble in water as well as in benzene.

Preparation of Methylated Ethylated Glycoluril

Into a suitable reaction vessel, equipped as before, there was introduced 142 parts (1 mole) of glycoluril and 300 parts (4.4 moles) of aqueous formaldehyde (44%), and the pH was adjusted to 7.5–8.0 with about 6 parts of 0.5 N NaOH solution. The reaction mixture was heated to 80° C. for 15 minutes. The pH of the reaction mixture was adjusted again with 0.5 N NaOH solution to about 7–7.5. The resultant pale yellow colored solution of tetramethylol glycoluril was distilled at 50° C. under reduced pressure until the weight of the syrup in the reaction vessel was between about 305–310 parts. To this syrup, 160 parts (5 moles) of methanol and 6 parts of concentrated nitric acid was added at 50° C. There was a slight exotherm after the addition. The reaction temperature was held at about 55°–60° C. for 30 minutes and later cooled to 22° C. and neutralized to a pH of 7–8 with a 20% NaOH solution. It was then slowly heated to 105° C. under reduced pressure to remove substantially all of the alcohol and water. To the resulting syrup, 92 parts (2 moles) of ethanol and 4 parts of nitric acid were added and the charge was heated to about 70° C. and the reaction mixture held at that temperature for 30 minutes. After cooling the reaction mixture to 22° C., it was neutralized to a pH of 7.5 using a 20% NaOH solution. The neutralized solution was heated slowly to 105° C. under reduced pressure, to remove all of the alcohol-water mixture. The resultant syrup was filtered hot at 80° C. to remove inorganic salts and other impurities. The yield of the syrup was 320 grams. The foil solids were 99.5% and the product was soluble in water. The nuclear magnetic resonance analysis indicated that the ratio of methoxy to ethoxy groups in the product was 1:0.63, respectively, i.e., on average degree of methylation of about 2.4 and degree of ethylation 1.6.

The procedure for the preparation of the methylated ethylated glycoluril was repeated in all essential details except that during the second alkylation step, 138 parts (3 moles) of ethanol were used. The final syrupy product was soluble in water. The foil solids were 99%. The nuclear magnetic resonance analysis indicated that the ratio of methoxy to ethoxy groups in the product was 1:0.81, respectively. The product was water-soluble and was also soluble in benzene.

Preparation of Methylated Butylated Glycoluril

The process for the preparation of the methylated ethylated glycoluril set forth hereinabove was repeated in all essential details except that the methylolated glycoluril was first reacted with 192 parts (6 moles) of methanol. The second alkylation was accomplished with n-butanol as follows: To the syrup obtained after the methylation step there was added 74 parts (1 mole) of n-butanol and 1 part of nitric acid, and the reaction mixture was heated to 105° C. for one-half hour, the distillate, which appeared to be methanol, was removed using a Dean-Stark trap. The pale yellow colored solution was cooled to 20° C. and neutralized to a pH of 7–7.5 with a 0.5 N NaOH solution. The unreacted butanol and any water in the reaction mixture were removed under reduced pressure at 121° C. The resultant approximately 100% solids viscous liquid was analyzed by N.M.R. and found to have a methoxy:butoxy ratio of 1:0.32 respectively, i.e., on average, degree of methylation of about 3, and degree of butylation 1.0. The product remains liquid and does not crystallize on storage at ambient temperature. The product was sparingly soluble in water but was soluble in benzene.

It has been indicated hereinabove that the glycoluril cross-linking agents of the present invention may be used to form coating compositions with a plurality of non-gelled polymeric materials such as the acrylic emulsions, as are disclosed in the U.S. Pat. Nos. 3,471,388, 3,661,819 as well as the 3,663,389. Certain polyols may be used with the glycoluril cross-linking agents of the present invention which polyols are disclosed in the U.S. Pat. Nos. 3,959,202 and 3,969,803. All of these cited patents are incorporated herein by reference in order to avoid unnecessary redundancy with respect to the types of polymeric materials with which the novel glycoluril cross-linking agents of the present invention may be used.

As a specific illustration of polymeric materials which can be used with the cross-linking agents of the present invention, the following are illustrative.

Acrylic Emulsion A

This emulsion is a commercially available acrylic emulsion polymer prepared by polymerizing a monomer blend of 55 parts of n-butyl acrylate, 30 parts of styrene, and 15 parts of acrylic acid. The emulsion has an acid number of 90–100 on a solids basis and a final solids content of about 48%.

Polyether Polyol Resin B

Polyether polyol B was prepared by reacting one mole of bisphenol A (4,4' isopropylidene diphenol) with 6 moles of ethylene oxide. The resulting product had a viscosity of 2,840 centipoises and a hydroxyl number of 215. The molecular weight of the polyether polyol B was about 520. Polyether polyol B is a liquid material.

Acrylic Resin C

Acrylic resin C is a commercially available anionic acrylic polymer, prepared by the standard polymerization techniques, in an inert organic solvent such as 2-ethoxyethanol in which 55 parts of n-butylacrylate, 30 parts of styrene, and 15 parts of acrylic acid are copolymerized. At the end of the polymerization, the resulting polymer is diluted to 75% solids with n-butanol. The average molecular weight of the polymeric material is about 10,000–20,000 and has an acid number of 115. This polymer is designed for water-based coatings and electrodepositions. At 75% solids and at 25° C., the polymer solution has a Gardner-Holdt viscosity of $Z_{6+}$.

Polyester Resin D

This oil free saturated polyester resin is commercially available and is prepared by reacting isophthalic acid, adipic acid and propylene glycol in a conventional esterification process. This polyester resin is identified as a saturated polyester resin inasmuch as it is free of non-benzenoid unsaturation. The polyester, designed for coil coating, has the following characteristics: it is organic solvent soluble; solids 70% in Solvesso 150, a high boiling hydrocarbon solvent; Gardner-Holdt viscosity (25° C.) $Z_1$–$Z_3$; acid number 10 maximum; hydroxy number 30.

The following examples are illustrative of the paint formulations that have been prepared by utilizing the mixed full ethers of the fully methylolated glycolurils of the present inventions in combination with various non-gelled polymeric materials.

EXAMPLE 1

Into a suitable mixing vessel, there was introduced 245 parts of Acrylic emulsion A, 95 parts of deionized water, 103 parts of dimethoxymethyl diethoxymethyl glycoluril, 308 parts of titanium dioxide pigment and 4.1 parts of dimethylaminoethanol and the components were then sand milled. After the pigment was properly dispersed, an additional 245 parts of the acrylic emulsion A were slowly added, followed by 0.72 part of p-toluene sulfonic acid dissolved in 1 part of isopropanol, 4.1 parts of dimethylaminoethanol, and 45 parts of deionized water. The resultant water-based high solids enamel had a Ford Cup No. 4 viscosity of 50 seconds at 25° C. at a solids content of 61%. The films were drawn down with a draw-blade on zinc phosphate pretreated cold-rolled steel panels, and they were cured at 175° C. for 20 minutes. The film properties were as follows:

| | |
|---|---|
| Film Thickness | 1.0 mil |
| Gloss, 60° | 92 |
| Gloss, 20° | 79 |
| Knoop Hardness | 14.4 |
| Pencil Hardness | H-2H |
| Reverse Impact Resistance, in.-lbs. | 0–10 |
| MEK Resistance (Double Rubs) | >200 |

The water-based enamel of Example 1, after aging at 55° C. for 21 days, had excellent stability. There was no pigment settlement and there was no change in the film properties of the coatings prepared from the aged enamel.

COMPARATIVE EXAMPLE 2

103 parts of tetramethoxymethyl glycoluril (a solid) was first dissolved in 188 parts of deionized water by heating the mixture to about 55° C. To this clear solution there was charged 245 parts of acrylic emulsion A and 308 parts of titanium dioxide pigment and 4.1 parts of dimethylaminoethanol. The mixture was then sand milled. After the pigment was properly dispersed, an additional 245 parts of acrylic emulsion A were slowly added, followed by 0.72 part of p-toluene sulfonic acid dissolved in 1 part of isopropanol and 4.1 parts of dimethylaminoethanol. The resultant water-based high solids enamel had a Ford Cup No. 4 viscosity of 50 seconds at 25° C. at a solids content of 59%. Films were drawn down on zinc phosphate pretreated cold-rolled steel using a 0.002 inch draw-blade and the films were cured at 175° C. for 20 minutes. The baked films had the following properties:

| | |
|---|---|
| Film Thickness | 1.1 mils |
| Gloss, 60° | 93 |
| Gloss, 20° | 92 |
| Knoop Hardness | 10.9 |
| Pencil Hardness | H-2H |
| Reverse Impact Resistance, in.-lbs. | 10–200 |
| MEK Resistance (Double Rubs) | >200 |

This high solids water-based enamel, when aged overnight at 25° C. showed that the tetramethoxymethyl glycoluril was crystallizing out. The coatings prepared from such an enamel were glossier when cured but were full of craters and pin holes. When the same water-based paint was heated up again to 55° C., it became homogeneous and coatings obtained from the hot enamel and cured at 175° C. were smooth, glossy and crater-free.

EXAMPLE 3

Into a high speed Cowles dissolver, there were dispersed 52.4 parts of polyether polyol resin B, 17.6 parts of acrylic resin C, 30 parts of dimethoxymethyl, diethoxymethyl glycoluril, 1.5 parts of dimethylethanolamine, 1.7 parts of diisopropanolamine and 85 parts of titanium dioxide pigment. To this dispersed pigment paste were added 0.8 part of n-dodecylbenzene sulfonic acid and 54 parts of deionized water. The resultant water-based high solids enamel had a Ford Cup No. 4 viscosity of 82 seconds at 25° C. The films were drawn down with a 0.002 inch draw-blade on zinc phosphate pretreated cold-rolled steel panels and some panels were cured at 150° C. for 20 minutes and separately other panels at 175° C. for 20 minutes. The film properties were as follows:

| Cure Schedule | 150° C./20 Minutes | 175° C./20 Minutes |
|---|---|---|
| Film Thickness | 1.25 mils | 1.25 mils |
| Gloss, 60° | 92 | 92 |
| Gloss, 20° | 72 | 72 |
| Knoop Hardness | 6.8 | 11.5 |
| Pencil Hardness | F-H | H-2H |
| Reverse Impact Resistance, in.-lbs. | 140+ | 100 |
| MEK Resistance (Double Rubs) | >200 | >200 |

The water-based high solids enamel of this Example 3 had good shelf stability. There were no significant changes in the film properties of the coatings prepared from the enamel after aging for three weeks at 55° C. Examples 1 and 3 set forth hereinabove show the advantages of having a watercompatible and organic solvent-compatible mixed ethers of tetramethylol glycoluril in coatings. For one thing, they are liquid and are resistant to crystallization on storage. Unlike the tetramethoxymethyl glycoluril, which is a solid, these liquid materials are easy to handle in the plant and are easy to utilize in paint formulations. Furthermore, they yield a more homogeneous and stable paint. In the examples pigmented paints were prepared. However, if desired, clear coatings can be prepared by omitting any solid coloring material. On the other hand, if transparent colored coatings are desired, appropriate dyes and transparent pigments can be utilized to produce transparent colored coatings.

EXAMPLE 4

On a three roll mill there were dispersed 199.4 parts of titanium dioxide pigment with 142.4 parts of Polyester Resin D. To 227.8 parts of the above grind, there were added an additional 119 parts of Polyester Resin D, 12.3 parts of the methylated, ethylated glycoluril (as prepared hereinabove), 0.7 part of p-toluene sulfonic acid, dissolved in 1 part of isopropanol. The mixture was diluted with 15.7 parts of n-butanol, 23.1 parts of Solvesso 150, 5.8 parts of Cellosolve acetate and 1.3 parts of diacetone alcohol. The total blend was thoroughly mixed on a mechanical shaker. The resultant solvent based paint was filtered through a flannel cloth of 5 micron pore size. The resultant paint had a Ford cup No. 4 viscosity of 87 seconds at 25° C. at a solids content of 72%. Films were drawn down with a 0.0015 inch draw-blade on a plurality of Alodine 1200S aluminum panels. The films were baked separately at 232° C. and 260° C. each for 60 seconds. The film properties were as follows:

| Cure temperature 60 seconds | 232° C. | 260° C. |
| --- | --- | --- |
| Film Thickness (mils) | 0.9 | 0.9 |
| Gloss 60° | 99 | 100 |
| 20° | 89 | 87 |
| Knoop hardness (KHN$_{25}$) | 7.6 | 11.7 |
| MEK Resistance, double rubs (passes) | 200+ | 200+ |
| Adhesion (cross-hatched) | Excellent | Excellent |
| T-bend (passes) | T-0 | T-0 |
| After oven bake, 60 seconds | | |
| Gloss, 20° (% Retention) | 89 | 90 |
| T-bend (passes) | T-0 | T-1 |

The accelerated stability of the paint at 55° C. after three weeks was excellent. There was no change in the properties of the baked films prepared from the paint aged at 55° C. for three weeks.

When the mixed ethers of the glycol derivatives of the present invention was used to form a coating composition with a non-gelled polymeric material, it is generally desired to use between about 2% and 50% by weight of the glycoluril derivative and correspondingly between about 98% and 50%, by weight, or the non-gelled polymeric material. It is preferred to use between about 10% and 40%, by weight of these novel glycoluril derivatives and correspondingly between about 90% and 60%, by weight, of the non-gelled polymeric material wherein these percentages are by weight based on the solids weight of these two components and the percentages total 100%.

The novel glycoluril derivatives of the present invention are so identified notwithstanding the fact that many of these derivatives used in this category will be simple, modified glycoluril compounds. On the other hand, some measure of self condensation may take place in the preparation of these novel glycoluril derivatives which will result in the production of polymeric materials such as dimers, trimers, tetramers, oligomers and the like which would put them in the category of condensation products or resinous materials. However, only lower molecular weight compounds, resinous materials or condensation products are preferred, namely, those that have a molecular weight between about 200 and about 2,000.

When the novel mixed ethers of the fully methylolated glycoluril derivatives are used in coating compositions with a non-gelled polymeric material, it is essential to make use of an acid catalyst. This catalyst will be used whether or not these glycoluril derivatives are used with the non-gelled polymeric material in an aqueous dispersion or in an organic solvent dispersion. The catalyst is used in an amount varying between about 0.05% to about 5.0%, by weight, based on the total solids weight of the glycoluril derivative and the non-gelled polymeric material. It is preferred to use between about 0.1% and 2.5%, by weight, of the acid catalyst, same basis. Among the preferred acid catalyst that may be used in the compositions of the present invention are trismethyl sulfonylmethane, trishexyl sulfonylmethane, p-toluene sulfonic acid, n-dodecyl benzene sulfonic acid, naphthylene sulfonic acid, dinonyl naphthylene sulfonic acid and the like. Reference is made to the U.S. Patent 3,960,688 which discloses the use of certain aromatic sulfonic acid compounds in electrodeposition processes utilizing certain non-gelled polymeric materials together with certain aminoplast crosslinking agents. This patent is incorporated herein by reference. The catalytic activity of an acid can also be generated in the coating compositions of the present invention by incorporating sulfonic acid groups into the polymeric material. This can be achieved by copolymerizing from about 0.1% to about 5.0% (based on the total monomer weight) of a monomer such as 2-sulfoethyl methacrylate, styrene sulfonic acid and the like. It is also possible to use alkyl esters of phosphoric acid or alkyl phosphonic acids as the acid catalyst in the coating compositions of the present invention.

Weaker organic acids such as formic acid, acetic acid, phthalic acid and the like may be used but are not preferred because they are not effective in promoting the cross-linking reaction at temperatures below 175° C. in a reasonable period of time such as less than about 30 minutes.

Inorganic acids such as nitric, sulfuric, phosphoric, hydrohalic, Lewis acids and the like may also be used.

In water-dispersible or water-dispersed coating compositions, if the polymeric material contains carboxylic acid groups, it is essential to use ammonia or a water-soluble organic amine in the composition in order to achieve the water-dispersibility of the total composition. The amount of ammonia or of the organic amine required is dictated by the amount of carboxylic acid groups present in the polymer. Normally, equivalent amounts of amine with respect to the carboxylic acid groups are sufficient to achieve water-dispersibility of the polymer and the coating composition. It is also possible to use only 10% to 20% of the equivalent amounts of amine with respect to the carboxylic acid groups of the polymer in order to achieve a water-dispersible composition. One can use ammonia or the water-soluble low molecular weight organic amines such as the primary, secondary or tertiary amines such as, for example, ethylamine, diethylamine, triethylamine, diethanolamine, N, N-dimethylethanolamine, diisopropanolamine and the like.

Although not required, in certain cases it may be helpful to make use of anionic or non-ionic surfactants to obtain stable water-dispersions of these organic coating compositions. The anionic surfactants, for example, can be sulfosuccinate, sodium dioctyl succinate, sodium cyclohexyl succinate and the like. A plurality of these anionic surfactants are available commercially. The non-ionic surfactants can be ethoxylated alkyl phenols and the like. The amount of the surfactant that is normally used is less than about 4%, by weight, based on the total paint solids weight.

Although the coatings of the present invention will principally be used to coat metals such as steel, aluminum and the like these coatings can also be used on other substrates such as wood, glass, plastics, paper, textiles and the like.

I claim:

1. A normally liquid, substantially fully mixed-alkylated, substantially fully methylolated glycoluril derivative consisting essentially of dimethoxymethyl diethoxymethyl glycoluril.

2. A composition of matter comprising a blend of from about 2% to about 50% by weight of a normally liquid, substantially fully mixed-alkylated, substantially fully methylolated glycoluril derivative which is essentially dimethoxymethyl diethoxymethyl glycoluril and correspondingly between about 98% and 50%, by weight of a non-gelled, polymeric material carrying an anionic charge, said polymeric material containing at least one class of reactive groups selected from the group consisting of carboxyl groups, alcoholic hydroxyl groups and amide groups, the amount of said groups in said polymeric material being at least about 0.5%, by weight, and not more than about 20%, by weight, based on the total weight of said polymeric material; said groups being reactive with said glycoluril derivative and said percentages of said glycoluril derivative and said polymeric material being based on the total weight of said glycoluril derivative and said polymeric material, said composition also containing from about 0.5% to about 5.0%, by weight, based on the total weight of said glycoluril derivative and said polymeric material, of an acid catalyst.

3. A composition according to claim 2 wherein said acid catalyst is p-toluene sulfonic acid.

* * * * *